United States Patent
Powers et al.

(10) Patent No.: US 7,074,976 B2
(45) Date of Patent: Jul. 11, 2006

(54) PROPYLENE PRODUCTION

(75) Inventors: Donald H. Powers, Pearland, TX (US); Robert S. Bridges, Friendswood, TX (US); Steven T. Coleman, Humble, TX (US)

(73) Assignee: Equistar Chemicals, LP, Houston, TX (US)

( * ) Notice: Subject to any disclaimer, the term of this patent is extended or adjusted under 35 U.S.C. 154(b) by 485 days.

(21) Appl. No.: 10/643,483

(22) Filed: Aug. 19, 2003

(65) Prior Publication Data

US 2005/0043574 A1 Feb. 24, 2005

(51) Int. Cl.
*C07C 6/04* (2006.01)

(52) U.S. Cl. .................................. 585/324; 585/644

(58) Field of Classification Search ............... 585/324, 585/332, 644
See application file for complete search history.

(56) References Cited

U.S. PATENT DOCUMENTS

| | | | | |
|---|---|---|---|---|
| 2,401,649 A * | 6/1946 | Leffer | ........................... | 208/70 |
| 3,326,866 A | 6/1967 | Haag | ......................... | 260/79.3 |
| 3,962,367 A | 6/1976 | Germanas et al. | ....... | 260/683.2 |
| 4,692,430 A | 9/1987 | Welch | ......................... | 502/342 |
| 4,962,267 A | 10/1990 | Slaugh | ........................ | 585/670 |
| 4,992,612 A | 2/1991 | Suzukamo et al. | ......... | 585/664 |
| 4,992,613 A | 2/1991 | Brownscombe | ............. | 585/666 |
| 5,898,091 A | 4/1999 | Chodorge et al. | ........... | 585/647 |
| 5,955,397 A | 9/1999 | Didillon et al. | ............. | 502/339 |
| 6,111,160 A | 8/2000 | Powers et al. | .............. | 585/671 |
| 6,323,384 B1 | 11/2001 | Powers et al. | .............. | 585/671 |
| 6,358,482 B1 | 3/2002 | Chodorge et al. | ........... | 422/189 |
| 6,495,732 B1 | 12/2002 | Hearn et al. | ................. | 585/664 |
| 6,743,958 B1 * | 6/2004 | Commereuc et al. | ....... | 585/324 |
| 2005/0124839 A1 * | 6/2005 | Gartside et al. | ............. | 585/643 |

OTHER PUBLICATIONS

R. L. Banks, *Journal of Molecular Catalysis*, vol. 8, p. 269-276, 1980, ISSN 0304-5102.

"Discovery and Development of Olefin Disproportionation (Metathesis)" by Robert L. Banks, American Chemical Society Symposium, Series, No. 222, Heterogeneous Catalysis: Selected American Histories, B.H. Davis and W. P. Hettinger, Jr., Editors, *American Chemical Society*, 1983, ISSN 0097-6156.

* cited by examiner

*Primary Examiner*—Walter D. Griffin
(74) *Attorney, Agent, or Firm*—Roderick W. MacDonald

(57) ABSTRACT

A method for making propylene from alpha olefins, internal linear olefins and isoolefins wherein the alpha olefins are subjected to a combination of hydrogenation and double bond isomerization to form additional internal linear olefins, the internal linear olefins are disproportionated with ethylene to form a propylene product, while the isoolefins are subjected to skeletal isomerization to form yet additional internal linear olefins to be converted into yet additional propylene.

15 Claims, 1 Drawing Sheet

PROPYLENE PRODUCTION

BACKGROUND OF THE INVENTION

1. Field of the Invention

This invention relates to a method for making propylene utilizing hydrocarbons that have four carbon atoms per molecule ($C_4$'s). More particularly this invention relates to a process for forming propylene from an isobutylene containing feedstock.

2. Description of the Prior Art

Although this invention will, for the sake of clarity of understanding, be described in the context of an olefin production plant (olefin plant), this invention is broadly applicable to the use, as feed thereto, of any hydrocarbon stream containing the requisite feed component(s) as described in detail herein.

Thermal cracking of hydrocarbons is a petrochemical process that is widely used to produce olefins such as ethylene, propylene, butenes, butadiene, and aromatics such as benzene, toluene, and xylene. In an olefin plant, a hydrocarbon feedstock such as naphtha, gas oil, or other fractions of whole crude oil is mixed with steam which serves as a diluent to keep hydrocarbon molecules separated. This mixture, after preheating, is subjected to severe hydrocarbon thermal cracking at elevated temperatures (1450° F. to 1550° F.) in a pyrolysis furnace (steam cracker).

The cracked effluent product from the pyrolysis furnace contains gaseous hydrocarbons of great variety (from 1 to 35 carbon atoms per molecule). This effluent contains hydrocarbons that are aliphatic, aromatic, saturated, and unsaturated, and can contain significant amounts of molecular hydrogen (hydrogen).

The cracked product of a pyrolysis furnace is then further processed in the olefin plant to produce, as products of the plant, various separate individual product streams of high purity such as hydrogen, ethylene, propylene, mixed hydrocarbons having four carbon atoms per molecule (crude $C_4$'s), and pyrolysis gasoline. It is this crude $C_4$ product of the edebutanizer of an olefin plant upon which is focused this description of one embodiment within this invention.

Crude $C_4$'s can contain varying amounts of n-butane (butane), isobutane, butene-1, butene-2, isobutylene (isobutene), acetylenes, butadiene, and hydrogen. The term butene-2 as used herein includes cis-butene-2, trans-butene-2, or a mixture of both.

Heretofore crude $C_4$'s have been subjected to butadiene extraction or butadiene selective hydrogenation to remove most, if not essentially all, of the butadiene and acetylenes present. Thereafter the crude $C_4$ raffinate was subjected to an etherification process wherein the isobutylene was converted to methyl tertiary butyl ether (MTBE).

Also heretofore crude $C_4$'s have been subjected to selective hydrogenation of dioelfins (butadiene) with simultaneous isomerization of alpha olefins (butene-1) to internal olefins (butene-2) followed by etherification of the isoolefins (isobutylene to MTBE), and finally metathesis of internal olefins (butene-2) with ethylene to produce propylene, see U.S. Pat. No. 5,898,091 to Chodorge et al.

In addition, catalytic distillation of various hydrocarbon streams for various purposes such as hydrogenation, monoolefin isomerization, etherification, dimerization, hydration, dissociation, and aromatic alkylation has been disclosed, see U.S. Pat. No. 6,495,732 B1.

Finally, olefinic $C_4$'s have been converted to propylene and isobutene using selective hydrogenation plus double bond isomerization of butene-1 to butene-2, followed by separation of isobutene from the butene-2, and metathesis of the butene-2 with ethylene to form propylene, see U.S. Pat. No. 6,358,482.

If MTBE market demand should decline, it is desirable to be able to utilize the isobutylene that was formerly used in producing MTBE to produce a different product that is enjoying more robust market demand.

It has been suggested that the isobutylene be dimerized to iso-octene followed by hydrogenation to iso-octane, or be alkylated to iso-octane, neither of which promises to be a cost-effective solution.

SUMMARY OF INVENTION

In accordance with this invention, not only are the internal olefins in a feedstock converted into propylene, but, in addition, the isobutylene in that feedstock and, depending on the recycle route chosen, the alpha olefins associated with such isobutylene are converted into additional internal olefins thereby substantially increasing the yield of propylene from a given (original) feedstock. This is a substantial advantage over and not suggested nor rendered obvious by the prior art. For example, U.S. Pat. No. 6,358,482 merely suggests that the isobutene recovered from its process can be used in various fashions. This is not a suggestion, even to one skilled in the art, to increase the yield of propylene from a specific feedstock by the skeletal isomerization of the isoolefins in that feedstock.

Other unobvious advantages for the process of this invention over the disclosures of the prior art will be described hereinafter in detail.

In the context of an olefin plant, an increase in the output of propylene product from that plant while using the same feedstock is a distinct advantage in a robust propylene market.

DESCRIPTION OF THE DRAWING

The sole FIGURE shows a schematic flow diagram of one embodiment within this invention.

DETAILED DESCRIPTION OF THE INVENTION

Figure 1:
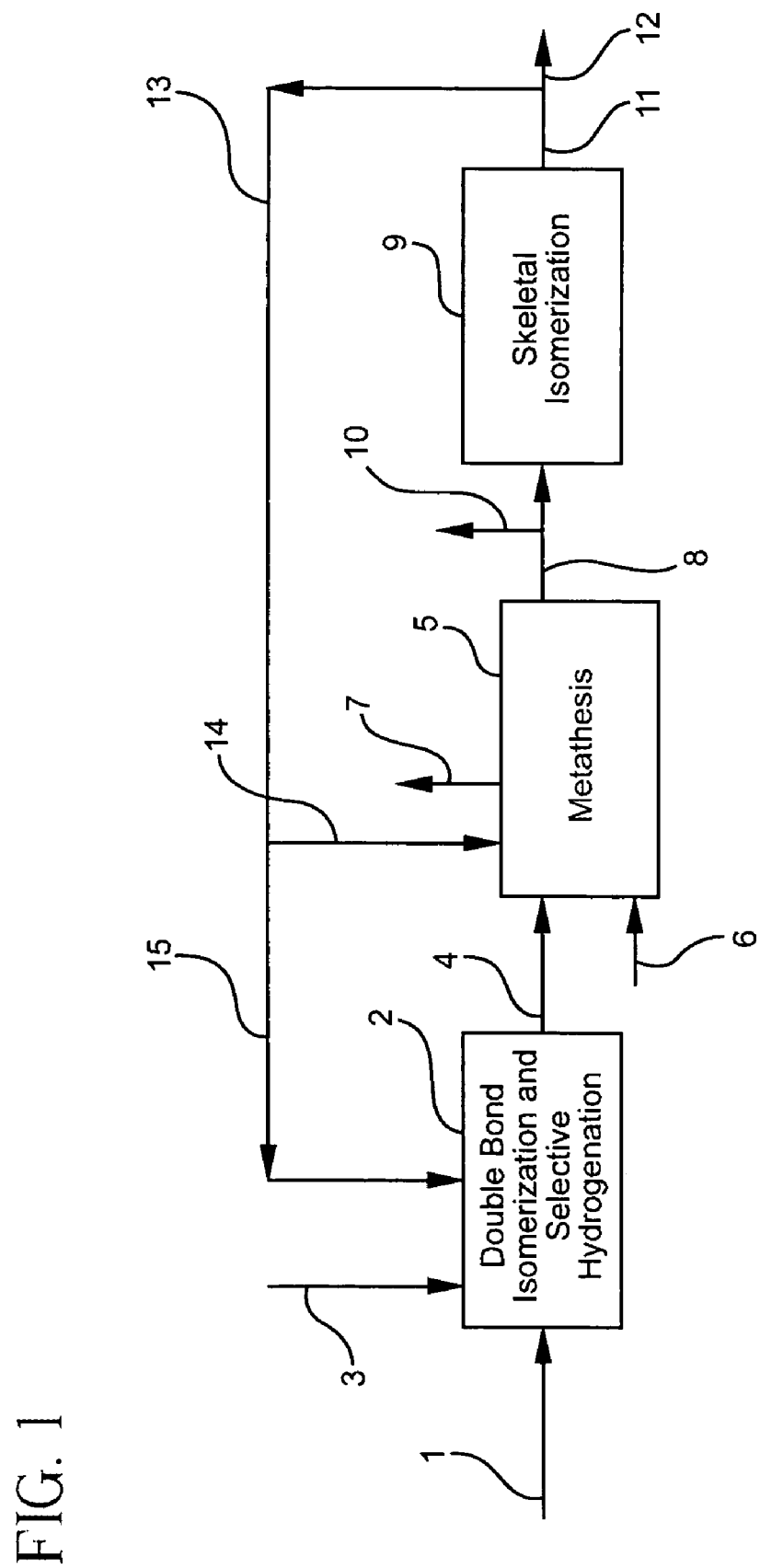

By this invention, and referring to the FIGURE, a feedstock 1 containing in whole or in part a first mixture composed of alpha olefins (linear alpha olefins), internal linear olefins (internal olefins), and isoolefins all having four carbon atoms per molecule is first subjected to a combination operation zone 2 wherein double bond isomerization conditions are present that convert (transform) at least part of the alpha olefins to internal linear olefins. At the same time diolefins and acetylenes present in the feedstock, if any, are selectively hydrogenated to produce, at least in part, additional alpha and internal linear olefins. Hydrogen is provided to zone 2 by way of line 3 for the selective hydrogenation part of the process of zone 2.

The product of operation 2 is a second mixture that is substantially enriched in internal linear olefins and essentially free of diolefins and acetylenes, but still contains isoolefins and alpha olefins. This product is passed by way of line 4 to a metathesis zone 5 wherein olefins are subjected to disproportionation conditions (metathesis). For example, internal linear olefins such as butene-2 in the second mixture in line 4 are passed to zone 5 wherein such olefins are subjected to disproportionation conditions in the presence of ethylene, provided by way of line 6, to form propylene. The propylene product of the process of this invention is recovered by way of line 7 for other disposition.

A third mixture containing unreacted linear olefins and isoolefins is recovered from zone 5 by way of line 8 and passed to skeletal isomerization zone 9 which maintains skeletal isomerization conditions that favor the conversion of isoolefins to a chemical equilibrium mixture of alpha olefins and internal linear olefins. A significant advantage of this invention is that this third mixture is substantially enriched in isoolefin content and depleted in internal olefin content. Thus, stream 8 has a very favorable ratio of isoolefins to alpha and internal linear olefins to allow skeletal isomerization operation 9 to function to form substantial additional quantities of alpha olefins and desirable internal linear olefins before reaching the normal chemical equilibrium constraints between isoolefins, alpha olefins, and internal linear olefins.

The product of zone 9 in line 11 is substantially enriched in internal linear olefin content over stream 8. At least part of this internal linear olefin content is new to and was not originally present in feedstock 1 thereby providing for the production of more (net) internal linear olefins than would be possible from feedstock 1 without the use of zone 9. This internal linear olefin enriched stream 11 which contains net production of internal linear olefins not in original feedstock 1, in turn provides for net production of propylene product 7 that would not otherwise have been recovered from the original chemical composition of feedstock 1.

Aliphatic compounds are not reactive in the process of this invention. A portion of stream 8 can be removed from the process by way of purge line 10, if desired, to relieve aliphatic, e.g., n-butane and/or isobutane, build up in the system. Stream 10 could be used for other purposes, for example, steam cracking of n-butane to ethylene, or an alkylation process. Alternatively or additionally, a portion of stream 11 could be taken by way of purge line 12 to relieve such aliphatic build up in the system. The hydrocarbon content of stream 11 would be better suited for an alkylation process than stream 8 because stream 11 contains a larger concentration of internal olefins. In addition, or alternatively, the fourth mixture in stream 12 could be employed in a known process that will alkylate its isoaliphatic content with the olefin content, such as alpha and internal $C_4$'s, to form an automotive gasoline alkylate of mixed isooctanes plus a separate $C_4$ stream product.

Stream 11 is a fourth mixture that can be returned as co-feed to (1) zone 2 by way of lines 13 and 15 for the conversion of at least part of its alpha olefin content to yet additional internal linear olefins that were not present in feedstock 1 and/or (2) zone 5 by way of lines 13 and 14 so that the net internal linear olefin content in stream 11 can be processed in zone 5 for net propylene production over that which was possible by utilizing feedstock 1 by itself and without benefit of the process of zone 9.

The feedstock (feed) or first mixture 1 for this invention can be any suitable stream that contains the requisite $C_4$ components. One such stream is a high purity isobutylene stream that contains no n-butane or isobutane. Such a stream can be obtained as a byproduct of a propylene oxide production process. This feed is passed into zone 2 which is a combination of a double bond isomerization zone (reactor) and a selective hydrogenation zone (reactor) so that the feed components, upon entering zone 2 are subjected in a single operation both to selective hydrogenation conditions, and double bond isomerization conditions in that zone.

Other suitable feeds include raffinate products obtained from the extractive distillation of crude $C_4$ product from an olefins plant with a solvent that preferentially removes diolefins such as butadiene by altering the relative volatility of the diolefins, or the selective hydrogenation of $C_4$'s to convert butadiene and acetylenes to butenes. These raffinate products (sometimes called raff-1 and super raff-1) are depleted (less than about 1 weight percent (wt. %), based on the total weight of the raffinate) in butadiene and acetylenes content, but rich (over 75 wt. % on the same basis) in a mixture of butene-1, butene-2, and isobutylene—all desired components for the process of this invention. The small amount of butadiene left in a raffinate product can be readily hydrogenated in zone 2.

Another suitable feed is a crude $C_4$ stream taken directly from an olefin plant debutanizer as described herein. This feed can require conventional hydrogenation of its butadiene and acetylenes content before it is passed into zone 2, because the butadiene content of the feed to zone 9 is preferably less than 100 parts per million (ppm).

In zone 2 alpha olefins such as butene-1 are transformed as to the location of their double bond without affecting the carbon atom skeleton (chain) thereof. Thus, straight chain (linear) butene-1 is converted to straight chain (linear) butene-2. This conversion proceeds up to the normal chemical equilibrium constraint of a mixture of alpha and internal olefins. Newly formed internal linear olefins are thus made available for conversion to propylene along with the internal linear olefins that were originally present in feedstock 1.

Zone 2 carries at least one catalyst effective for double bond isomerization. This same catalyst system can also be effective as a selective hydrogenation catalyst which promotes not only double bond isomerization, but also hydrogenation of diolefins and acetylenes at least in part to monoolefins if hydrogen is available. Hydrogen can be added to the process, if insufficient hydrogen is present in feedstock 1, by way of line 3 up to about 1 wt. % based on the total weight of the feed, greater amounts of hydrogen tending to reduce the selectivity of the catalyst for selective hydrogenation of diolefins and acetylenes. For example, while an alpha olefin such as butene-1 is converted at least in part to an internal linear olefin such as butene-2 in zone 2, at the same time butadiene and acetylenes such as vinyl acetylene are selectively hydrogenated to a mixture of net butene-1 and butene-2. Butadiene is selectively hydrogenated to butene-1 which makes additional butene-1 that is available for double bond isomerization in zone 2 to butene-2. This contributes to making net propylene production in zone 5.

The resulting reaction product is the second mixture in line 4 which is rich in, for example, butene-1 and butene-2, but with significant amounts of isobutylene, and containing essentially no butadiene or acetylenes. Second mixture 4 can also contain either or both of unreactive n-butane and isobutane if originally present in feed 1. Stream 4 is passed into metathesis zone 5.

In zone 5 butene-2 and ethylene co-feeds are metathesized to propylene product, 1 mole of butene-2 and 1 mole of ethylene yielding 2 moles of propylene. By the use of catalysts known in the art in zone 5, some double bond isomerization of butene-1 to butene-2 can be achieved in that zone, if desired.

Stream 8 is passed to zone 9 for the conversion of isoolefins such as isobutylene to an equilibrium mixture of monoolefins, i.e., butene-1 and butene-2, thereby producing new (net) butene-2, in addition to that which was produced in zone 2, for later conversion to additional net propylene by way of zone 5.

The product of zone 9 is the fourth mixture in line 11 which can contain one or more of alpha olefins, linear internal olefins, unconverted isoolefins and aliphatics. Fourth mixture 11 is useful in and returned to either or both of zones 2 and 5 by way of lines 15 and 14, respectively. If recycle is by way of line 15, additional net linear internal olefins are formed in zone 2. Ultimately these net linear internal olefins are transformed into net additional propylene in zone 5. If recycle is by way of line 14, net additional propylene is formed in zone 5.

It should be noted here that, in this invention, skeletal isomerization in zone 9 is distinguished from double bond isomerization in zone 2 in that skeletal isomerization involves the movement of a carbon atom to a new location on the carbon atom skeleton of the molecule, e.g., from a branched isobutylene skeleton to a linear or straight chain (not branched) butene skeleton. Double bond isomerization does not involve movement or shifting of carbon atoms on the skeleton, but rather only involves movement of a double bond within the existing skeleton while the carbon atoms that form the carbon atom skeleton remain in their original locations in that skeleton.

Stream 11 can, in whole or in part, be recycled as co-feed to zone 2 such as by introduction into stream 1 and/or metathesis zone 5 such as by introduction into stream 4. This way, butene-2 that was not disproportionated with ethylene in its first pass through zone 5 is returned to the process for another pass through that zone.

The selective hydrogenation/double bond isomerization conditions within zone 2 can be a temperature of from about 70° F. to about 300° F. and a pressure of from about 20 psig to about 560 psig and a weight hourly space velocity of from about 0.5 $h^{-1}$ to about 20 $h^{-1}$.

The catalyst or catalysts used in zone 2 can vary widely. If there is no appreciable (less than about 100 ppm) butadiene content in feed 1, the catalyst can be primarily only an isomerization component and need not contain a component (catalyst) that promotes the hydrogenation of butadiene. If there is appreciable butadiene content in the feed (greater than about 100 ppm and up to about 1 wt. % based on the total weight of the feed), the catalyst can additionally contain a hydrogenation component. If butadiene is present in the feed, the isomerization catalyst and hydrogenation catalyst can be employed in zone 2 either mixed with one another in a single catalyst bed in zone 2, or in separate discrete catalyst beds in zone 2, each discrete bed containing either solely isomerization catalyst or solely hydrogenation catalyst, or a dual function catalyst as explained herein below.

The isomerization catalyst employed in zone 2 effects and favors the formation of internal linear olefins over the formation of linear alpha olefins. Generally, the catalysts employed promote, preferably primarily promote, double bond shifts within a specific olefin molecule (double bond isomerization). The catalysts useful in this invention will be obvious to one skilled in the art since they are either commercially available or fully disclosed in the prior art. Such catalysts include acidic ion exchange resins such as sulfonated resins with sulfonic acid sites (U.S. Pat. No. 3,326,866), perfluorinated polymer sulfonic acid catalyst, phosphoric acid catalyst, carboxylic acid catalyst, fluorinated alkyl sulfonic acid catalyst, alumina plus alkali metal (U.S. Pat. No. 4,992,612), zinc aluminate (U.S. Pat. No. 4,692,430), zirconia, sulfated zirconia, cobalt/sulfur catalyst (U.S. Pat. No. 3,962,367), ruthenium oxide (U.S. Pat. No. 4,962,267), alumino phosphates, and zeolite structures with or without alkali metal (U.S. Pat. No. 4,992,613), and alumina or silica alumina.

The hydrogenation catalyst component employed in zone 2 favors the saturation with hydrogen of at least one, preferably one, double bond in a butadiene molecule, and similar saturation or partial saturation of acetylenes. These catalysts will also be obvious to one skilled in the art and commercially available. Such catalysts can contain a noble metal, e.g., at least one of palladium, platinum, and rhodium, either supported or unsupported. When the noble metal is supported on an acidic material, a combined (dual) function catalyst of double bond isomerization and selective hydrogenation is achieved. Suitable catalysts having both a double bond isomerization and a hydrogenation capability will be obvious to those skilled in the art, and include, but are not limited to, at least one of palladium, platinum, and rhodium carried on an acidic support such as alumina, silica alumina, and the like. The noble metal(s) can be present in the catalyst in amounts of from about 0.1 to about 0.3 wt. % based on the total weight of the catalyst. For other suitable catalysts for both hydrogenation and double bond isomerization, see U.S. Pat. Nos. 5,955,397 and 6,495,732 B1.

The metathesis zone 5 operating conditions can vary widely, but are generally a temperature of from about 300° F. to about 800° F., a pressure of from about 200 psig to about 600 psig, and a weight hourly space velocity of from about 1.0 $h^{-1}$ to about 100 $h^{-1}$.

Suitable catalysts that promote, preferably primarily promote, metathesis as described herein are known in the art, and include at least one of halides, oxides and/or carbonyls of at least one of molybdenum, tungsten, rhenium and/or magnesium carried on a support such as silica and the like. The conversion of butene-2 in the presence of excess ethylene to propylene is known and has been demonstrated; see R. L. Banks, Journal of Molecular Catalysis, Vol. 8, p. 269–276, 1980, ISSN 0304-5102. For more information on olefin metathesis, see Discovery and Development of Olefin Disproportionation (Metathesis) by Robert L. Banks, American Chemical Society Symposium Series, No. 222, Heterogeneous Catalysis: Selected American Histories, B. H. Davis and W. P. Hettinger, Jr., Editors, American Chemical Society, 1983, ISSN 0097-6156.

The skeletal isomerization zone 9 operating conditions also vary widely, but generally are a temperature of from about 450° F. to about 1200° F., a pressure of from about 0 psig to about 150 psig, and a weight hourly space velocity of from about 1.0 $h^{-1}$ to about 50 $h^{-1}$. Skeletal isomerization catalysts useful in this invention are known in the art and include zeolites having one-dimensional pore structures with a pore size ranging from greater than about 0.42 nanometers (nm) and less than about 0.7 nm. This type of isomerization process is known, see U.S. Pat. No. 6,111,160 to Powers et al., and U.S. Pat. No. 6,323,384 also to Powers et al.

EXAMPLE

A raffinate-1 stream from a butadiene extraction unit consisting essentially of about 3 wt. % isobutane, about 40 wt. % isobutylene, about 27 wt. % butene-1, about 16 wt. % butene-2, about 1 wt. % butadiene, and about 13 wt. % n-butane, all wt. % based on the total weight of the stream, is employed as feed 1 to zone 2 shown in the drawing with a double bond isomerization/hydrogenation catalyst bed carried in zone 2. The isomerization conditions are about 200° F. and about 220 psig. The double bond isomerization/ hydrogenation catalyst is a commercially available catalyst composed of 0.2 wt. %, based on the total weight of the catalyst, of palladium on a silica/alumina support.

In zone 2, butene-1 is transformed to butene-2, and the newly formed butene-2 is employed as additional feed material for the metathesis reaction in zone 5. Butadiene is selectively hydrogenated in zone 2 to butene-1.

A mixture of n-butane, isobutane, isobutene, butene-1 and butene-2 containing about 40 wt. % butene-2, based on the total weight of the mixture, is removed from zone 2 and passed by line 4 to metathesis zone 5 wherein it is contacted with a molar excess of ethylene in the presence of a commercially available metathesis catalyst composed of a mixture of tungsten oxide and magnesium oxide at a temperature of about 625° F. and pressure of about 400 psig. Two products are recovered from zone 9, a propylene stream at 11, and a separate stream 8 of n-butane, isobutane, isobutylene, butene-1, and a depleted amount of butene-2 as compared to feed 1 and stream 4.

Newly formed butene-1 from butadiene hydrogenation, existing butene-1 that was not converted to butene-2, unreacted butene-2, isobutane, and isobutylene are recovered and transferred by way of line 8 to skeletal isomerization zone 9.

In zone 9 the primary reaction is the transformation of branched isobutylene to linear butenes (-1 and -2). A secondary reaction is double bond isomerization of butene-1 to butene-2. Accordingly, the product 11 of zone 9 is a mixture of butene-2 (newly formed and unconverted), butene-1, unconverted isobutylene, n-butane, and isobutane. This product is enriched in newly formed butene-2 that was not in feed 1, and is recycled by way of lines 13 and 15 as co-feed to zone 2 to make yet more butene-2 from butene-1, and ultimate use of both existing and newly formed butene-2 in the metathesis operation 9 thereby producing net additional propylene product. The isobutylene in recycle stream 13 ultimately reaches skeletal isomerization zone 9 again at which time at least part of it is converted to a mixture of butenes (-1 and -2).

On a single pass basis, and with no recycle, about 65 wt. percent of the butene-2 in stream 4 is converted to propylene, with about 88 percent selectivity to propylene. In the skeletal isomerization operation, also on a single pass basis, there is about a 30 wt. percent conversion of isobutylene with an 80 percent selectivity to butene-1 and butene-2.

It can be seen from the foregoing example that the process of this invention is replete with opportunities throughout the entire process to make newly formed net butene-2 which is then made into net propylene product.

Accordingly, it can be seen that the process of this invention is highly leveraged toward and very efficient in making new butene-2. Thus, in addition to making propylene out of the butene-2 originally in the feedstock to the process, this invention significantly increases the amount of propylene product obtained from a given feed based on the butene-2 content of the original feed.

Reasonable variations and modifications are possible within the scope of this disclosure without departing from the spirit and scope of this invention.

We claim:

1. A method for forming propylene comprising providing a feedstock containing at least in part a first mixture of hydrocarbons comprising alpha olefins, internal linear olefins, and isoolefins having four carbon atoms per molecule, introducing said feedstock into a combination hydrogenation/double bond isomerization zone wherein (1) any diolefins and acetylenes that may be in said feedstock are converted at least in part to alpha and internal linear olefins, and (2) at least part of said alpha olefins in said feedstock and at least part of said alpha olefins formed by said hydrogenation are converted to additional internal linear olefins thereby producing as a product of said combination zone a second mixture that is enriched in internal linear olefins, passing said second mixture directly into a metathesis zone which favors the disproportionation of internal olefins with ethylene to produce propylene as a product of the process, recovering from said metathesis zone a third mixture separate from said propylene product that contains at least in part alpha olefins, internal olefins, and isoolefins, passing said third mixture into a skeletal isomerization zone wherein said isoolefins are converted at least in part to additional internal linear olefins to form a fourth mixture that is enriched in internal linear olefins, returning said fourth mixture as co-feed to at least one of said combination zone and said metathesis zone for the production of at least one of additional internal linear olefins in said combination zone and additional propylene in said metathesis zone.

2. The method of claim 1 wherein said fourth mixture is returned as co-feed to said metathesis zone.

3. The method of claim 1 wherein said first mixture contains at least in part butene-1, butene-2, and isobutylene, said combination zone contains at least one catalyst that promotes the hydrogenation of butadiene and acetylene and the formation of butene-2 from butene-1, said metathesis zone contains at least one catalyst that promotes the disproportionation of butene-2 with ethylene to form propylene, said skeletal isomerization zone contains at least one skeletal isomerization catalyst that promotes the conversion of isobutylene to a mixture of butene-1 and butene-2, said mixture of butene-1 and butene-2 along with any unconverted isobutylene being recovered from said skeletal isomerization zone as said fourth mixture.

4. The method of claim 3 wherein said combination zone operating conditions are a temperature of from about 70° F. to about 300° F., a pressure of from about 20 psig to about 560 psig, and a weight hourly space velocity of from about 0.5 $h^{-1}$ to about 20 $h^{-1}$.

5. The method of claim 3 wherein at least one of diolefins and acetylenes are initially present in said feed stock and are hydrogenated in said combination zone at least in part to additional butene-1 and butene-2.

6. The method of claim 3 wherein said metathesis zone operating conditions are a temperature of from about 300° F. to about 800° F., a pressure of from about 200 psig to about 600 psig, and a weight hourly space velocity of from about 1 $h^{-1}$ to about 100 $h^{-1}$.

7. The method of claim 3 wherein said skeletal isomerization operating conditions are a temperature of from about 450° F. to about 1,200° F., a pressure of from about 0 psig to about 150 psig, and a weight hourly space velocity from about 1 $h^{-1}$ to about 50 $h^{-1}$.

8. The method of claim 3 wherein said combination zone catalyst is at least one of palladium, platinum, nickel, and rhodium carried on an acidic support.

9. The method of claim 4 wherein said metathesis zone catalyst is at least one of halides, oxides, and carbonyls of at least one of molybdenum, tungsten, rhenium, and magnesium carried on a support.

10. The method of claim 3 wherein said skeletal isomerization zone catalyst is at least one zeolite having one dimensional pore structures with a pore size ranging from greater than about 0.42 nm and less than about 0.7 nm.

11. The method of claim 1 wherein said feedstock contains, in addition to said first mixture, butadiene, vinyl acetylene, n-butane, isobutane, and hydrogen; in said combination zone said butadiene is at least partially hydrogenated to additional butene-1; in said metathesis zone butene-2 is used in the making of propylene to make said third mixture depleted in butene-2 content; and in said skeletal isomerization zone additional butene-2 is formed to make said fourth mixture enriched in butene-2 for return to the process to convert at least part of said butene-2 in said fourth mixture into additional propylene.

12. The method of claim 10 wherein said fourth mixture is employed as co-feed to said metathesis zone.

13. The method of claim 10 wherein a purge stream containing at least one of butane, butene-1, butene-2, and isobutane is removed from at least one of said third mixture and said fourth mixture.

14. The method of claim 13 wherein said purge stream is employed in an alkylation zone to form an alkylate of mixed isooctanes.

15. The method of claim 14 wherein said mixed isooctanes are gasoline grade.

* * * * *